United States Patent [19]
Wiesman

[11] Patent Number: 5,983,661
[45] Date of Patent: Nov. 16, 1999

[54] CONTAINER ARRANGEMENT AND METHOD FOR TRANSPORTING EQUINE SEMEN

[76] Inventor: Jon P. Wiesman, 5470 Mt. Pisgah Rd., York, Pa. 17406

[21] Appl. No.: 09/200,758

[22] Filed: Nov. 27, 1998

Related U.S. Application Data

[60] Provisional application No. 60/066,925, Nov. 28, 1997, and provisional application No. 60/072,746, Jan. 27, 1998.

[51] Int. Cl.⁶ ........................................ F25D 3/08
[52] U.S. Cl. ........................... 62/457.1; 62/371; 62/457.2
[58] Field of Search ................................. 62/457.2, 371, 62/457.1

[56] References Cited

U.S. PATENT DOCUMENTS

| | | |
|---|---|---|
| 83,316 | 10/1868 | Rankin . |
| 111,950 | 2/1871 | Lester . |
| 991,715 | 5/1911 | Good . |
| 1,369,367 | 2/1921 | Thomson . |
| 1,512,945 | 10/1924 | Norcross . |
| 2,216,202 | 10/1940 | Lake . |
| 2,315,425 | 3/1943 | Hill et al. . |
| 2,496,296 | 2/1950 | Lobl . |
| 2,652,698 | 9/1953 | Schlumbohm . |
| 2,662,520 | 2/1953 | McMahon . |
| 2,673,454 | 3/1954 | Gallie et al. . |
| 2,989,856 | 6/1961 | Telkes . |
| 3,108,840 | 10/1963 | Conrad et al. . |
| 3,156,105 | 11/1964 | Bahner . |
| 3,238,002 | 3/1966 | O'Connell et al. . |
| 3,303,662 | 2/1967 | Moline et al. . |
| 3,309,893 | 3/1967 | Heffler et al. . |
| 3,395,550 | 8/1968 | Dungan . |
| 3,654,773 | 4/1972 | White . |
| 3,766,008 | 10/1973 | Macomber . |
| 3,810,367 | 5/1974 | Peterson . |
| 3,855,816 | 12/1974 | Miller . |
| 3,938,346 | 2/1976 | Ovchinnikov et al. . |

(List continued on next page.)

OTHER PUBLICATIONS

A. T. Francl et al., "Motility and Fertility of Equine Spermatozoa in a Milk Extender After 12 or 24 Hours at 20+20 C.," *Theriogenology*, vol. 27 (No. 3):517–525, Mar. 1987.

D. D. Varner et al., "Fertilizing Capacity of Equine Spermatozoa Stored for 24 Hours at 5 or 20+20 C.," *Theriogenology*, vol. 32 (No. 4):515–519, Oct. 1989.

(List continued on next page.)

*Primary Examiner*—Henry Bennett
*Assistant Examiner*—Mark Shulman
*Attorney, Agent, or Firm*—McDermott, Will & Emery

[57] ABSTRACT

In order to simply and safely transport a sample of semen, the semen is mixed and diluted with a dual sugar (sucrose and glucose) extender in a ratio of up to 10:1 (v/v) by inducting the semen into a semen storage device, e.g., a large volume syringe, having extender therein and optionally disposed within a form-fitting, radiation blocking, sleeve. The semen storage device is placed on a support member located on the floor of a rigid foamed plastic container and covered with a thermoregulating plate also made of a rigid foamed plastic. A refrigerant pack with solid foam coolant is placed on top of the thermoregulating plate, and the container is closed using a lid having a central boss that fits snugly into the mouth of the container, and further has a continuous ridge that fits into a recess formed in the upper edge of the container. The closed container is then placed in a light weight double-walled cardboard box that exhibits considerable structural strength, increases the insulation, absorbs ambient moisture and protects the rigid foamed plastic container during transit. The cooling rate achieved by the present invention is no more than about 0.20° C./min, preferably about 0.10° C./min, and most preferably about 0.01° C./min, over a temperature range of about 38° C. to about 5° C., preferably from about 15° C. to about 5° C. The optimum transport temperature of the semen sample during transport is preferably about 5° C. to about 10° C., most preferably about 7.5° C. to about 8.5° C.

20 Claims, 9 Drawing Sheets

U.S. PATENT DOCUMENTS

| | | |
|---|---|---|
| 3,940,943 | 3/1976 | Sikes et al. . |
| 3,942,668 | 3/1976 | Eberle et al. . |
| 3,943,993 | 3/1976 | Smith . |
| 3,948,409 | 4/1976 | Ovchinnikov et al. . |
| 4,055,268 | 10/1977 | Barthel . |
| 4,134,276 | 1/1979 | Lampard . |
| 4,145,895 | 3/1979 | Hjerstrand et al. . |
| 4,154,363 | 5/1979 | Barthel . |
| 4,199,022 | 4/1980 | Senkan et al. . |
| 4,262,494 | 4/1981 | Karow, Jr. ............................ 62/384 |
| 4,292,817 | 10/1981 | Loucks . |
| 4,311,022 | 1/1982 | Hall . |
| 4,322,954 | 4/1982 | Sheehan et al. ...................... 62/371 |
| 4,347,713 | 9/1982 | Morrison et al. . |
| 4,530,816 | 7/1985 | Douglas-Hamilton ................ 422/1 |
| 5,236,088 | 8/1993 | Dhority et al. ...................... 206/438 |
| 5,355,684 | 10/1994 | Guice .................................. 62/54.2 |

OTHER PUBLICATIONS

D. H. Douglas–Hamilton et al., "A Field Study of the Fertility of Transported Equine Semen," *Journal of Theriogenology*, vol. 22 (No. 3), Sep. 1984.

T. Katila et al., "Comparison of Three Containers Used for the Transport of Cooled Stallion Semen," Department of Large Animal Medicine and Surgery, *Theriogenology*, vol. 48:1085–1092, 1997.

"The Hamilton System: Intelligent Breeding by choice, not location.", Hamilton Equine Systems, Inc.

B.W. Pickett et al., "Chapter 8, Effect of Seminal Extender, Storage Time and Temperature on Fertility," *Procedures for Collection, Evaluation and Utilization of Stallion Semen for Artificial Insemination*, Sep. 1987.

W.R. Allen et al., "The Current Position of A.I. in Horse Breeding," *Equine Veterinary Journal*, 8(2): 72–74 (1975).

Y. Nishikawa, "Studies on the Preservation of Raw and Frozen Horse Semen," *J. Reprod. Fert., Suppl.*, 23:99–104 (1975).

M. Tischner, "Results of Artificial Insemination of Horses in Poland in the Post–War Period," *J. Reprod. Fert., Suppl.*, 23:111–114 (1975).

D.S. Demick et al., "Effect of Cooling, Storage, Glycerolization and Spermatozoal Numbers on Equine Fertility," *Journal of Animal Science.*, vol. 43, (No. 3):633–637 (1976).

W.L. Cooper, "Artificial Breeding of Horses," *Sumposium on Reproduction Equine*, vol. 2, (No. 2):267–275 Nov. 1980.

J.P. Hughes, et al., "Artificial Insemination in the Equine. A Comparison of Natural Breeding and Artificial Insemination of Mares Using Semen from Six Stallions," Departments of Clinical Sciences and Animal Husbandry, University of California, May 2, 1969.

Eric W. Swanson et al., "A Satisfactory Method of Shipping Dairy Bull Semen Long Distances," *Journal of Dairy Science*, vol. 27:143–146 (1944).

H.A. Herman et al., "Transporting and Shipping Semen," *The Artificial Insemination of Dairy Cattle, A Handbook and Laboratory Manual*, 46–47 (1947).

Enos J. Perry et al., "The Shipping of Semen," *The Artificial Insemination of Farm Animals*, Chap. 16:303–308 (1947).

Enos J. Perry et al., "The Shipping of Semen," *The Artificial Insemination of Farm Animals*, Chap. 16:374–376 (1968).

E. Klug et al., "Results of Insemination of Mares with Fresh and Frozen Stallion Semen," *J. Reprod. Fert., Suppl.* 23:107–110 (1975).

CONTAINER ARRANGEMENT AND METHOD FOR TRANSPORTING EQUINE SEMEN

RELATED PATENT APPLICATIONS

This application is based on U.S. provisional patent application Ser. Nos. 60/066,925, filed Nov. 28, 1997, and 60/072,746, filed Jan. 27, 1998, the entire disclosures of which are incorporated herein by reference.

FIELD OF THE INVENTION

The present invention generally relates to a thermally insulated transport container arrangement and method for using same to transport equine semen. More specifically, the present invention relates to an inexpensive, self-contained, thermally insulated, disposable, refrigerated transport container arrangement that can greatly extend the length of time over which the spermatozoa of equine semen can be maintained motile and fertile, and thus render it possible to effectively transport this type of material over long distances.

BACKGROUND OF THE INVENTION

Transporting semen (germplasm), e.g., equine or canine semen, is beneficial to breeders for several reasons. Shipping semen is less costly than transporting female horses or dogs to an unfamiliar facility. Stress and risk of disease are minimized when female horses or dogs can remain at home. Further, using artificial insemination allows a stallion to service more mares than he could using natural service, and allows the stallion to continue to show or perform during the breeding season. When shipped semen is handled properly, pregnancy rates approach those achieved using natural service. Semen destined for transport is collected from a male, examined and cooled for shipment. The development of conventional systems allowing controlled cooling has been instrumental. The advantages of using cooled semen make it a valuable addition to breeding programs and has been used to increase the genetic pool in many breeds.

However, numerous factors influence pregnancy rates achieved when mares are bred with transported, cooled stallion semen. For instance, sperm are very sensitive to many environmental factors, including temperature, light, physical trauma, and a variety of chemicals. Any factor that impacts the ability of sperm to resist environmentally-induced damage will adversely affect fertility achieved when using cooled transported semen. Semen must be handled from collection to insemination in such a manner as to not shock nor damage the sperm. If collection or storage devices are contaminated by bacteria, chemicals, or even soap residue, the survivability of the sperm cells can be severely diminished. Proper temperature control of semen prior to cooling and prior to insemination is crucial. For example, if semen is initially mixed with extender that is too cool or too warm, damage will likely occur.

Mares will ovulate 24 to 48 hours before the end of heat and pregnancy rates from cooled stallion semen are the highest when mares are inseminated within 24 hours following semen collection. Some stallion semen is still highly viable up to 48 hours following collection. Semen transported and stored for up to 72 hours may appear to have good motility, but fertilization capabilities are typically poor. Thus, when it is required to transport equine semen samples over long distances or even overseas, it is typically necessary to maintain the motility and fertility of the spermatozoa for 48 hours, at the very minimum, and ideally for more than 72 hours, in order that samples reach its destination and can be effectively used. However, until the development of the present invention, it has been virtually impossible, when using conventional postal/courier services, to achieve this. More specifically, although semen specimens can be transported for such prolonged periods of time if special motorized refrigeration units are used, the costs of such apparatus and the weight penalties incurred when air mail/freight is involved, are prohibitive. Thus, there has been a long felt need for an inexpensive and disposable container that is self-contained (viz., passively cooled) and sufficiently light to enable ready dispatch by conventional delivery/mail services.

One example of a passively cooled, self-contained transportation container, that has been proposed to transport equine semen is disclosed in U.S. Pat. No. 4,530,816 issued to Douglas-Hamilton on Jul. 23, 1985. In this arrangement, which has been marketed under the name Equitainer™, the specimen is enclosed in a plastic bag and placed in a metal cup in a manner wherein it is sandwiched between bags of liquid, such as water, which act as so called thermal ballast. The lower portion of the container is filled with a refrigerant can filled with ice or gelatinized ice. A thermal insulating layer, made of a vulcanized rubber, is disposed between the refrigerant (ice) and the metal cup (made of copper sheet $\frac{1}{32}$" thick, for example) in which the sample and the thermal ballast bags are disposed. The '816 patent discloses that the optimum steady state temperature is close to, but slightly greater than, 0° C., and in a temperature range of from 4° C. to 10° C. When the semen specimen, which is enclosed in a plastic bag, is placed in the metal cup, it is allowed to cool at a rate of 0.3° C./min until the temperature of the specimen reaches about 5° C., it may be stored for about 30 hours.

Spermatozoa from most animal species are susceptible to irreversible damage if exposed to a sudden drop in temperature, also known as "cold shock." It is known that stallion spermatozoa are more susceptible to cold shock than bovine, ovine, or porcine spermatozoa. Cold shock is generally considered to be the result of rapid cooling from 20° C. to 8° C. It is known that semen can be cooled relatively quickly from about 37° C. (99° F.) down to about 20° C., but must be slow cooled at a rate of .05 C°/min from 20° C. to 5° C. (47° F.). The above described and other shipping containers have been developed which purport to cool stallion semen at a correct, prescribed rate. Generally, these conventionally available containers generally cool semen over a 10 hour period, and hold the semen at 5° C. (47° F.). It is suspected that the cooling rate achieved by these devices is, in at least a certain temperature range, too rapid, and undesirable "cold shock" frequently occurs to a portion of a semen specimen. During the development of the present invention, however, it was discovered that, after the temperature of collected semen has fallen to about 15° C., the sensitivity of the semen to cold shock is heightened. In overlooking this fact, it is believed that conventionally available containers undesirably reduce the viability of semen samples transported/stored therein.

Of the factors believed to influence the length of time over which viable semen specimens can be successfully transported, water is particularly toxic and exposure to even small amounts of moisture is highly injurious to semen. The fact that the preferred refrigerant disclosed in the '816 patent is ice or a mixture of ice and gelatin water, is also suspected to have an adverse effect on the longevity of a semen sample transported therein, particularly after the ice melts and assumes a fluid liquid form. A drawback with this prior art arrangement is that it tends to promote the accumulation of substantial amounts of condensation, such as water, which not only aggravates the problems associated with the spilt/extended semen (causing objectionable odors, and providing an environment in which various types of microorganisms may spawn and render it very difficult to maintain aseptic conditions), but, as mentioned above, also effectively functions as a powerful spermicide. Accordingly, during transport this condensate can seep into the container in which the semen is stored, and present a serious risk of catastrophic damage to the semen sample. It is also noted that plastic thermal ballast bags of the kind disclosed in the container of the '816 patent are filled with a colored liquid that has a high thermal inertia (high heat capacity) as does water. Leakage of these containers, which may occur during a rough transit, and/or poor storage/handling by the end user prior to disposition in the container, also presents the same problem because condensate tends to accumulate.

One attempt to improve upon the arrangement disclosed in the '816 patent took the form of a foamed plastic container that was marketed under the name Equine Express™. This arrangement provided a simple plug-like door and a commercially available bottle type of refrigerant pack that was placed in the container on top of a thermal insulating layer which was interposed between the refrigerant pack and the samples. However, this arrangement proved to be unable to cool and maintain the sample in the required condition for more than about 45 hours, as is shown in test results reported herein.

Accordingly, there remains a need for a container that allows for transporting samples of equine semen over long distances while at the same time maintaining the motility and fertility of the transported spermatozoa for at least 48 hours without the attendant disadvantages of conventionally available containers and methods.

SUMMARY OF THE INVENTION

It is an object of the present invention to provide an arrangement that enables the shipment of equine semen over long distances, including shipment overseas, wherein delays often occur, e.g., at customs and at any of multiple transfers between different modes of transport.

It is a further object of the present invention to provide an arrangement that enables an equine semen sample to be maintained in a motile and fertile condition for spermatozoa for a prolonged period of at least three days from the time of collection.

It is another object of the present invention to provide an arrangement which enables the economic transport of a highly degradable material, such as equine semen, in a disposable, totally self-contained, passively cooled, inexpensive container that has essentially no moving parts, and that is not equipped with elaborate thermostatically controlled cooling arrangements or the like, for periods of time approximating at least about three and a third days.

It is yet another object of the present invention to provide an arrangement that is both disposable, capable of receiving approval from the USDA-APHIS, and which can be properly sealed and used for intercontinental transit, for example.

The above and other objects are accomplished by a container arrangement for transporting semen, such as equine semen, comprising:

at least one semen storage device or container for storing equine semen;
a rigid foamed plastic container comprising:
an interior with a bottom;
a floor located on the bottom of the interior;
at least one support member contoured to support the at least one semen storage device;
an upper end; and
an upper edge located at the upper end and containing a recess therein extending continuously thereabout for receiving at least one ridge extending from a lid, the lid for closing the upper end of the rigid foamed plastic container when it is open, wherein the lid is formed with at least one ridge that extends continuously about a lower surface of the lid proximate an edge of the lid, wherein the at least one ridge is adapted to be received in the recess of the rigid foamed plastic container in a manner that forms a seal when the lid is pressed onto the upper end of the rigid foamed plastic container;
a refrigerant pack containing a solid foam coolant; and
a separating means disposed in the interior of the rigid foamed plastic container for separating the at least one semen storage device from the refrigerant pack, and for limiting the cooling rate of the at least one semen storage device, when containing an equine semen sample, to no more than about 0.20° C./min over at least the temperature range of about 38° C. to about 5° C.

The present invention is also directed to a method for transporting semen, such as equine semen, comprising the steps of:

mixing an extender solution with a sample of equine semen to form an extended semen mixture, wherein the extender solution has a pH and an osmolality, each of which has been previously adjusted to within a respective predetermined range;
introducing at least a portion of the extended semen mixture into at least one semen storage device and capping the semen storage device;
placing the at least one semen storage device on at least one support member provided therefore in the bottom of a rigid foamed plastic container, wherein each support member is contoured to accept at least one semen storage device;
placing a ported thermoregulating plate in the rigid foamed plastic container in a manner which partitions the interior of the container into a lower compartment in which the semen storage device is disposed, and an upper compartment in which a refrigerant pack containing a solid foam coolant is disposed, wherein the thermoregulating plate is formed of a rigid foamed plastic, and overlays the at least one support member formed in the bottom of the rigid foamed plastic container in a manner that closes each port so as to restrict fluid communication between the upper and lower chambers;
applying a lid to the rigid foamed plastic container in a manner that closes an upper end of the rigid foamed plastic container, wherein the lid comprises a rigid foamed plastic material, at least one sealing rib which extends about a lower surface of the lid that is snugly received in a recess which extends continuously about the upper end of the rigid foamed plastic container; and
enclosing the rigid foamed plastic container with the lid closed in place in a corrugated cardboard box.

Further, the present invention is directed to a container arrangement comprising:
a single corrugated cardboard blank adapted to be folded into a double-walled box having a single site of entry;

a plastic strip embedded in the cardboard blank and extending a full length of the blank;

first and second holes formed in the blank in a manner wherein the first and second holes pass through the plastic strip, and are located proximate first and second ends of the cardboard blank; and the first and second holes are located proximate one another when the double-walled corrugated cardboard blank is folded into its box configuration in a manner that permits a lead to be passed therethrough to enable the double-walled corrugated box to be locked against unauthorized entry.

The combination of some or all of the above-mentioned features exhibits is effective for storing/transporting semen for up to at least 77 hours. In addition, upon arrival at its destination, the amount of time that is required between opening the foamed plastic container and actually injecting the semen during an insemination is minimal. Thus, the present invention, ensures that the spermatozoa are delivered to the actual point of use with minimum degradation.

Additional objects and attendant advantages of the present invention will be set forth, in part, in the description that follows, or may be learned from practicing or using the present invention. The objects and advantages may be realized and attained by means of the instrumentalities and combinations particularly pointed out in throughout this description and the appended claims. It is to be understood that the foregoing general description and the following detailed description are exemplary and explanatory only and are not to be viewed as being restrictive of the invention, as claimed.

BRIEF DESCRIPTION OF THE DRAWINGS

The accompanying drawings, which are incorporated in, and constitute a part of the specification, illustrate embodiments of the present invention and, together with the description, serve to explain the principles of the present invention.

DETAILED DESCRIPTION OF PREFERRED EMBODIMENTS

Figure 1:
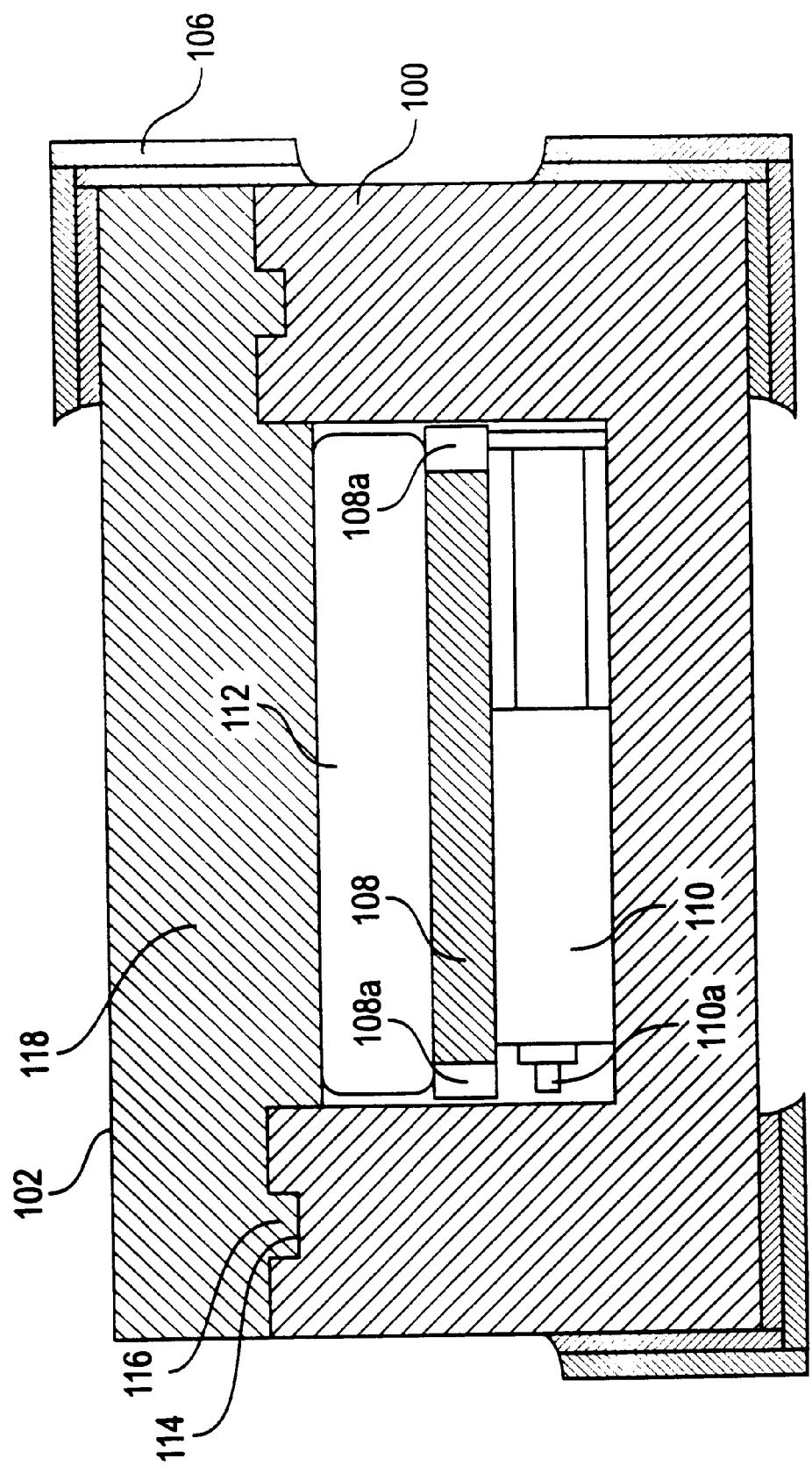
FIG. 1 is a schematic side sectional view showing an embodiment of the rigid foamed plastic container of the present invention in a fully assembled state.
Figure 2:
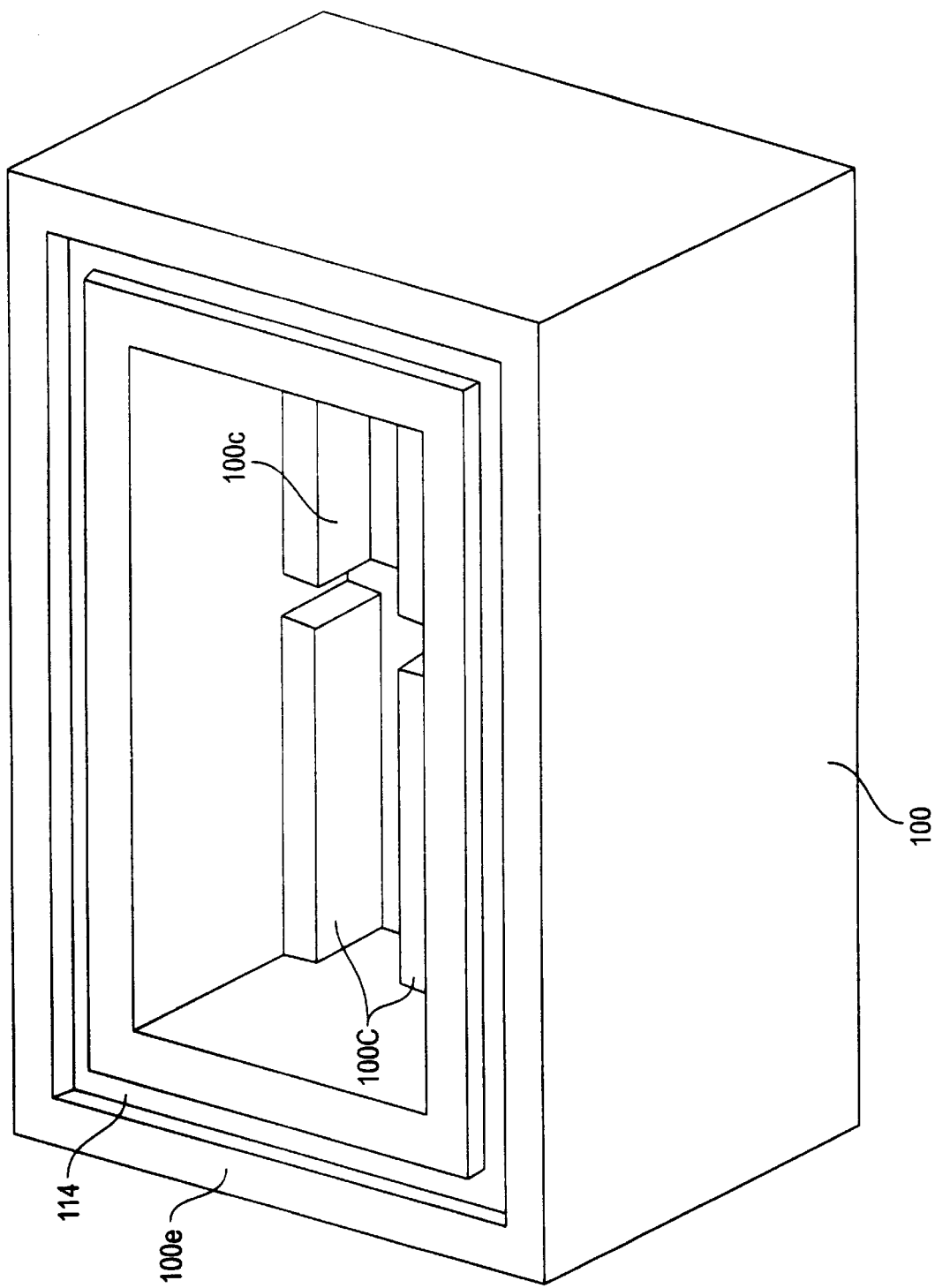
FIG. 2 is a perspective view showing details of the rigid foamed plastic container, which forms a vital part of the invention.

All patents, patent applications and literatures cited in this description are incorporated herein by reference in their entirety. In the case of inconsistencies, the present disclosure, including definitions, will prevail.

The present invention is directed to a relatively inexpensive, passively cooled, transport container arrangement/system for overcoming the difficulty of maintaining the required motility/fertility/viability of spermatozoa for a time sufficiently long enough to permit the samples to be transported over long distances, including shipping to overseas markets. In other words, to ship such a sample to distal market sites, it is necessary, even with modern transport, to maintain spermatozoa motility/fertility for 72 hours or more. During the development of the present invention, it was realized that there were several factors that had a clear bearing on the required longevity, and that must be considered to achieve the required length of transportability time.

Among these different factors, the amount of time that is wasted at the beginning and end of the transportation of semen specimens was recognized to be important. The time required to move a semen sample to a bench, add extender prior to placing it in a transport container, as well as the time for other operations relating to unpacking and preparation for insemination, must be taken into consideration.

Moreover, one of the measures that is taken into account in the practice of the present invention is the use of an extender, the pH and osmolality of which are balanced prior to mixing with a semen sample. This reduces the time for which the semen is exposed to detrimental influences such as light, atmospheric moisture, and the like, and enables the semen to be placed in a container or semen storage device as quickly as is practical. Unextended semen, maintained at it's collection temperature (99° F.) for over 15 minutes results in markedly reduced sperm motility at 24 hours. Therefore, semen must be collected, filtered, analyzed for volume, motility, and concentration, mixed with a suitable extender, and placed in the a shipping container within 15 minutes.

Use of an extender solution with semen processed for storage and transport is critical in its survivability. Extender provides nutrients to the sperm cells and contains antibiotics to destroy harmful bacteria. Because of reduced viability, it is believed that mares should be inseminated with 1 to 2 billion sperm cells and a volume of not more than 40 ml of semen. If a stallion has a sufficient concentration, the ejaculate may be split and several shipments obtained from a single collection. A further feature is the use of an extender that contains both sucrose and glucose. While the exact degree and mechanism by which the use of this type of dual sugar extender is effective in prolonging the life of the sperm during transit has not been determined with any certainty, is preferred over conventional single sugar types of extenders. The amount of extender used is also important. The preferred amount of dilution with the present invention is greater than with the prior art, and can be as high as 6:1 or more (e.g., 10:1). By way of example, a dual sugar semen extender that can be used in accordance with the present invention may be formulated, without limitation, as follows:

| | |
|---|---|
| Nonfat dry milk solids (from Sanalac, e.g.) | 24.0 gram |
| Glucose | 26.5 gram |
| Sucrose | 40.0 gram |
| Potassium Penicillin G (Sigma #P7794) | 1,000,000 units |
| Amikacin Sulfate (Sigma #A2324) | 1 gram |
| Cell culture tested water (Gibco #15230-147) | q.s. to 1000 cc |

After thoroughly mixing the above ingredients, the pH and the osmolality are adjusted using an aqueous solution of sodium bicarbonate until the pH falls in the approximate range of about 6.85–7.0 and the osmolality exhibits a value in the approximate range of about 350–365 mOsm/l. Alternatively, it is possible to add a suitable amount of dry sodium carbonate powder or crystals directly to the above formulation once the appropriate amount is accurately determined.

Examples of antibiotics that may be added to an extender used in accordance with the principles of the present invention include, without limitation, penicillin G, streptomycin, gentamicin sulfate, ticarillin, polymyxin B sulfate, etc. Penicillin G typically contains approximately 1600 units per milligram; thus, a typical quantity is about 625 mg. For each gram of solid material is used, approximately 1 cc of water is subtracted from that which is required to produce the final volume of 1000 cc. The inclusion of gram positive and gram negative antibiotics in the semen extender solution enhances the success of the insemination that is carried out after transportation to a destination. As previously mentioned, both of these types of microorganisms are found in the reproductive tracts of male and female horses, and the proliferation of such contaminating bacteria during transit can have a detrimental effect on the insemination, as well as lead to an abortion inducting infection in the recipient mare. In addition, adjustment of the pH and osmolality of the semen extender solution prior to mixing with the semen has the clear advantage of reducing the amount of time over which the delicate semen sample is exposed to deleterious effects.

Possibly the single most critical factor affecting the motility, fertility, viability, and longevity of spermatozoa of semen samples is the cooling rate of a semen sample once placed in a transport container. In particular, the present invention is based, in part, on the observation that semen samples that are protected against cold shock, and that are stored at a reduced temperature, tend to survive longer than samples that are maintained at room temperature. Although it has been recognized that slow cooling rates may be important in maintaining the longevity of a semen sample, the phases of the cooling have heretofore not been addressed. Rapidly cooling in a temperature range of about 20 to about 15° C. has little detrimental effect on the motility/fertility of spermatozoa. However, below about 15° C., the rate of cooling has a marked injurious effect. In fact, it has been discovered during the development of the present invention that a cooling rate of less than about 0.20° C./min after the temperature of the sample has lowered to about 15° C., is essential to prolonging the effective insemination life of equine semen samples. Even slower cooling rates after the temperature is reduced to about 15° C., e.g., preferably no more than about 0.10° C./min, most preferably about 0.01° C./min, provide better chances for maintaining the motility/fertility of spermatozoa over long periods of time. The achievement of such a slow rate of cooling, followed by a prolonged maintenance of an optimum transport temperature (e.g., preferably about 5° C. to about 10° C., most preferably about 7.5° C. to about 8.5° C.) was found to be extremely difficult to achieve in a passively cooled environment, i.e., without the use of powered refrigerating devices. Efforts to insulate the sperm samples from the refrigerant in order to slow the cooling rate, while allowing the efficient use of the refrigerant over a prolonged period, often met with failure. The task was rendered even more difficult when attempting to achieve an economically viable cost per unit by using a simple, inexpensive, disposable, self-contained, passive refrigerant package.

To overcome this problem, the present invention preferably uses a refrigerant/cooling pack as a coolant. Although any suitable coolant or refrigerant capable of achieving a cooling rate within the above parameters may be used in accordance with the principles of the present invention, a solid foam-type coolant was found to be preferred. This type of coolant permits the overall cooling rate to be lowered below that possible with phase change types of coolants/refrigerants such as ice. An example of a preferred coolant that can be used in accordance with the principles of the present invention is a foam brick coolant (MCC FPP31, commercially available from the Midlands Chemical Company). This preferred coolant was found to exhibit the slowest thawing, and is capable of remaining colder for longer periods of time compared to a variety of other types of refrigerants tested. Moreover, the preferred coolant contains a foamed material that is constantly solid, and does not undergo any perceptible solid-liquid phase change as heat is absorbed thereby. In other words, the preferred solid foam refrigerant is unlike frozen water, for which the change from a solid state (i.e., ice) to a molten state (i.e., water) follows a scenario that reflects certain physical chemical characteristics of water; namely, the solid-to-liquid transition of water first exhibits a powerful heat absorbing capacity as the ice converts to water, followed by a secondary, much reduced heat absorbing capacity as the cold water absorbs more heat. The only shortcoming found with the MCC FPP31 refrigerant pack was that it required a slightly longer period to freeze than other commercially available refrigerants tested. While capable of providing the critical cooling rate, the MCC FPP31 solid foam refrigerant was also found to exhibit another advantage. If the pack in which the foam brick is enclosed is compromised during transit, the problem of toxic liquid water running loose in the container is totally eliminated.

When the preferred coolant pack is combined with a thermoregulating plate that separates the refrigerant from the semen samples, it is possible to enhance the full potential of the present invention. The plate may be ported so as to permit relatively free insertion of an operator's fingers to permit ready removal of the plate. In addition, ribbing, in the form of support/partition members, may be incorporated on the inside bottom of a rigid foamed plastic container to close off the ports and prevent unrestricted fluid communication between the respective chambers storing the semen sample (s) and the refrigerant pack. Any suitable material, thickness and density of the thermoregulating plate made of any suitable material may be used to control the amount of heat that is transferred to the solid foam refrigerant/coolant pack (to cause cooling), to prevent the spermatozoa from being cooled at an undesirably excessive rate. Because the preferred solid foam cooling pack exhibits a flatter curve of heat absorption versus temperature, i.e., it does not undergo a phase change with a concomitant large change in heat capacity, it was discovered that the ported thermoregulating plate can be thinner than the plates used to protect spermatozoa in prior art devices that utilized solid-to-liquid phase change coolants. A thinner ported thermoregulating plate also prevents over insulation, which otherwise tends to defeat effective cooling once the coolant has completely converted to the liquid phase, with its lower cooling capacity.

Further, the lid of the rigid foamed plastic container may be formed from any suitable material, e.g., a rigid foamed plastic such as polystyrene or polyurethane. In accordance with the present invention, such a lid is formed with at least one continuous rib that extends about the periphery of the lower side of the lid. This rib is arranged to be received in a recess that continuously extends about an upper edge at the upper end of the rigid foamed plastic container. The sealing effect of this lid design is believed to be of importance in the overall effectiveness of the present invention.

Unexpectedly, the present invention eliminates the problem of condensation formation within the container during transit. Without wishing to be bound by the following theory, it appears that the slow cooling rate that results from the use of a solid foam coolant (MCC FPP31), in combination with the sealing effect provided by the rib/recess at the lid/container interface, is responsible for the overall success of the present invention. In various other comparative arrangements that were tested, it was found that placing the coolant above the samples induced the problem of condensation formation, which tended to leak down into the area of the stored sample containers. Of course, such an arrangement produced the real danger that water (viz., the condensate) would seep into an imperfectly sealed container (s) and cause at least partial spoilage of the sample(s) contained therein.

A further factor that is believed to contribute to the success of the present invention resides in the semen storage device in which the semen samples are stored during transit. It is critical that the semen storage devices be both sterile and free of any chemicals or compounds that have spermicidal activity, or that otherwise could have any kind of negative effect on the longevity of spermatozoa stored therein. In accordance with the principles of present invention, preferred semen storage devices include, without limitation, sterile plastic syringes or free standing tubes made of polypropylene with caps. Use of such semen storage devices in accordance with the present invention requires selection of a size (volume handling capacity) that is sufficient to accommodate a large quantity of extender that may be added therein in proportion to the quantity of semen thereby permitting the mixing of an increased volume of extender with a given volume of spermatozoa/semen. The beneficial effects of using larger syringes and relatively greater volumes of sugar extender include, without limitation, (1) a smaller surface area for a given volume of semen, which attenuates the cooling rate of the contents, and (2) the immediate use of the material for insemination upon the opening of the container. Preferred sizes include, without limitation, from about 10 ml to about 225 ml, with a more preferred size being about 50 ml.

Further, it is known that exposure to radiation in the visible light, ultraviolet or x-ray ranges can have a detrimental effect on the viability of cooled semen. To overcome this problem, the semen storage device can be opaque or fitted with a disposable, removable, and form-fitting protective sleeve/tube that is capable of preventing harmful light, UV or x-ray radiation from penetrating the semen storage device and reaching the contents therein. The form-fitting sleeve may be made of any suitable material or combination of materials so long as it is capable of blocking harmful radiation from reaching the semen stored within the semen storage device. In a preferred embodiment, the form-fitting sleeve is a tube or cylinder that is disposed around the semen storage device and has a reflective foil layer affixed to the inner and outer sides of the tube. Unexpectedly, it has been discovered that use of a form-fitting sleeve is advantageous because it further attenuates/slows the cooling rate of the stored semen during transport.

Further, an extender solution is preferably added to dilute a semen sample contained the semen storage device of the present invention. As mentioned above, use of an extender enhances longevity of a sperm's motility, provides vital nutrients, increases the volume of the inseminate thereby allowing for the insemination of more than one mare, helps protects spermatozoa from extreme environmental changes that occur while cooling (including thermal shock and toxic materials that produced upon the death of a spermatozoa), and reduces bacterial contamination of the sperm. The amount of dilution with an extender is preferably about 3:1 to about 10:1, more preferably about 4:1, most preferably about 6:1 (v/v). Within this range, the cascade effect, which can kill an entire initially viable semen sample, has been found to be greatly reduced or eliminated. Preferably, the extender contain at least two different sugars, which is believed to have a positive effect on spermatozoa longevity. Further, because both gram positive and gram negative microorganisms are found in the reproductive tracts of stallions and mares, an antibiotic may be added to the extender to promote successful insemination carried out after transport. It has been realized that semen contaminating gram positive and gram negative bacteria proliferate during storage and transport, and potentially not only diminish the viability of the spermatozoa, but also may lead to abortion inducing infections in recipient mares.

More specifically, the present invention resides in a container arrangement/system for transporting equine semen comprising:

at least one plastic syringe or polypropylene tube with cap containing equine semen; a container made of a rigid foamed plastic material, the rigid foamed plastic container including a support structure for supporting the at least one plastic syringe or polypropylene tube;

a lid for closing an open upper end of the container, the lid being formed with at least one ridge which extends continuously about a lower surface of the lid proximate an edge of the lid, the ridge being adapted to be received in a recess which extends continuously about an upper edge of the rigid foamed plastic container in a manner which forms a seal when the lid is pressed onto the rigid foamed plastic container;

a refrigerant pack containing a solid foam coolant; and a separating means disposed in the rigid foamed plastic container for separating the at least one plastic syringe or polypropylene tube from the refrigerant pack, and for limiting the cooling rate of the syringe to no more than about 0.20° C./min, preferably no more than about 0.10° C./min, most preferably about 0.01 ° C./min, in a temperature range of about 15° C. to about 5° C.

In this embodiment, the separating means comprises a ported thermoregulating plate disposed in the interior of the rigid foamed plastic container to separate a lower chamber in which the support members (which also serve as partition members) are formed and in which the plastic syringe(s) and/or polypropylene tube(s) is supported, and an upper chamber in which the refrigerant pack containing the solid foam coolant is disposed, the thermoregulating plate having first and second ports formed therein at opposite ends of the thermoregulating plate, the first and second ports being arranged to overlay a support/partition member, and thus be closed in a manner which restricts fluid communication between the upper and lower chambers.

In this preferred embodiment, the semen sample is diluted with an extender solution containing sucrose, glucose, dry skim milk, and preferably at least two selected antibiotics— one being effective against gram positive bacteria and the other being effective against gram negative bacteria. The semen sample is inducted into a syringe which preferably holds from about a 10 ml to about a 225 ml aliquot, more preferably about a 50 ml aliquot, of extender solution. The semen sample is diluted at the very least with about 3 parts of extender, preferably at least about 4 parts of extender, and more preferably about 6 to about 10 parts of extender. Shipping volumes of extended semen in a semen storage device (e.g., plastic syringe or polypropylene tube with cap) range in size from about 10 ml to about 225 ml in the practice of the present invention. A typical volume is about 50 to about 60 ml.

In another preferred embodiment, the present invention is directed to a container arrangement for transporting equine semen comprising:

a thermally insulated rigid container made of a recyclable foamed plastic material, the rigid foamed plastic container including support members formed on a floor thereof, the support members being adapted to support at least one plastic syringe or polypropylene tube with cap containing extended equine semen;

a lid for closing an open upper end of the rigid foamed plastic container, the lid being formed with at least one ridge which extends continuously about a lower surface of the lid proximate an edge of the lid, the ridge being adapted to be received in a recess which extends continuously about an upper edge of the rigid foamed plastic container in a manner which forms a seal when the lid is pressed onto the rigid foamed plastic container;

a ported thermoregulating plate disposed in the rigid foamed plastic container to separate the interior thereof into a lower chamber in which the support members are formed and in which the syringe or polypropylene tube is supported, from an upper chamber in which a refrigerant pack containing a solid foam coolant is disposed, the ported thermoregulating plate having first and second ports formed therein, the first and second ports being formed at opposite ends of the thermoregulating plate and in positions wherein, when the thermoregulating plate is disposed in the container in a manner wherein it rests atop of one or more support members, the first and second ports are each located over a support member so that fluid communication between the upper and lower chambers is restricted; and a double-walled corrugated cardboard box snugly enclosing the rigid foamed plastic container and lid.

In this preferred embodiment, the ported thermoregulating plate is selected to attenuate the rate of cooling of the equine semen contained in the at least one plastic syringe or polypropylene tube with cap to no more than about 0.20° C./min, preferably no more than about 0.10° C./min, most preferably about 0.01° C./min over a temperature range from about 38° C. to about 5° C., and especially from about 15° C. to about 5° C.

The double-walled corrugated cardboard box tends to act as a wick to absorb ambient moisture before it can reach the rigid foamed plastic container, and, thus, in effect, act as a vapor barrier to attenuate the invasion of water vapor into the rigid foamed plastic container. The double-walled structure also endows the corrugated cardboard box with a very high level of structural integrity, which is believed to contribute substantially to the commercial viability of the present invention. In other words, the box is inexpensive and disposable, but still is able to protect the insulating container from damage which is apt to occur during transit via commercial carrier/postal services. The lid used in the above arrangement is formed with a central boss portion that is adapted to fit snugly into a mouth of the upper end of the rigid foamed plastic container. Further, the first and second ports are so dimensioned as to permit the insertion of digits, such as human fingers, to additionally permit the thermoregulating plate to be quickly and easily lifted from the position in which it separates the rigid foamed plastic container into upper and lower chambers.

In a further preferred embodiment, the present invention resides in a method for transporting equine semen, the method comprising the steps of:

mixing an extender solution having a pH and an osmolality which have been previously adjusted to within respective predetermined ranges, with a sample of equine semen;

inducting at least a portion of the mixture into a semen storage device (syringe, plastic tube/bottle with a cap) and then closing the semen storage device;

placing the syringe in the bottom of a thermally insulated container made of a foam plastic material;

placing a ported thermoregulating plate in the foamed plastic container in a manner which separates the interior of the foamed plastic container into a lower compartment in which the syringe is disposed, and an upper compartment in which a container containing a constantly solid, foamed refrigerant is disposed, the thermoregulating plate being formed of a foamed plastic having a predetermined thickness and density;

closing the ports in the thermoregulating plate by seating the thermoregulating plate on support/partition members which are formed in the inside bottom of the foamed plastic container, which are used to support the syringe in a stable position in the container, and which are located so that the ports are closed when the thermoregulating plate is in a seated position;

closing the container with a lid which closes an upper end of the foamed plastic container, and which is formed with at least one sealing rib which extends about the lower surface of the lid, the sealing rib being dimensioned so as to be snugly received in a groove which extends continuously about the upper end of the foamed plastic container; and enclosing the foamed plastic container and lid in a corrugated cardboard box. In this method, a suitable syringe is selected and has a surface area/volume ratio sufficiently low to attenuate the rate of cooling of the equine semen sample, and provide an increased volume for extender fluid to be mixed with the semen sample. The extender preferably comprises sucrose, glucose, dry skim milk, at least one antibiotic, and cell culture tested water, plus any chemicals (e.g., sodium carbonate or sodium bicarbonate) required to adjust the pH and/or osmolality of the extender fluid.

In still another preferred embodiment, the present invention resides in a container arrangement comprising:

a single corrugated cardboard blank adapted to be folded into a double walled box having a single site of entry;

a plastic strip which is embedded in the cardboard blank at manufacture and which extends a full length of the blank; and first and second holes formed in the cardboard blank in a manner wherein the first and second holes pass through the plastic strip and are located proximate first and second ends of the cardboard blank;

the first and second holes being located proximate one another when the cardboard blank is folded into its box configuration so that a lead or other attachment means can be passed therethrough to enable the box to be locked against unauthorized entry, and also provide a user knowledge that the box has been entered without permission. In one embodiment of the present invention, the cardboard may be treated with a water impermeable or resistive substance, e.g., wax, to create a vapor barrier to prevent undesired entry of moisture into the container arrangement.

This preferred embodiment of the present invention may further comprise:

a rigid foamed plastic container, including a unitary support structure for supporting at least one storage vessel, and being so dimensioned as to be receivable in the double-walled box;

a lid for closing an open upper end of the rigid foamed plastic container, the lid being formed with at least one ridge that continuously extends about a lower surface of the lid proximate an edge of the lid, the ridge being adapted to be received in a recess which extends continuously about an upper edge of the rigid foamed plastic container in a manner which forms a seal when the lid is pressed onto the rigid foamed plastic container; a refrigerant pack containing a solid foam coolant; and means disposed in the bottom of the rigid foamed plastic container for partitioning the interior thereof, separating the at least one storage vessel from the refrigerant pack, and for limiting the cooling rate of contents in the storage vessel to a value that is preferably no more than about 0.10° C./min, and more preferably about 0.01° C.

Turning now to the figures, FIGS. 1–12 show a preferred embodiment of the present invention. FIG. 1 depicts the arrangement in a fully assembled state. As shown, this arrangement includes a foamed plastic container 100, which is closed by a lid 102 that also is formed of foamed plastic. Foamed plastic container 100 and lid 102 are enclosed within a double-wall corrugated cardboard container 106, only parts of which are shown for illustrative simplicity.

Figure 9:
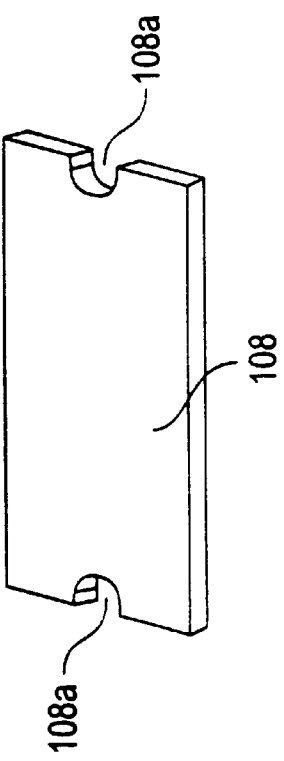
FIG. 9 is a perspective view of a ported thermoregulating plate, which is disposed in the rigid foamed plastic container to define a lower storage chamber and an upper refrigerant chamber.
Figure 12:
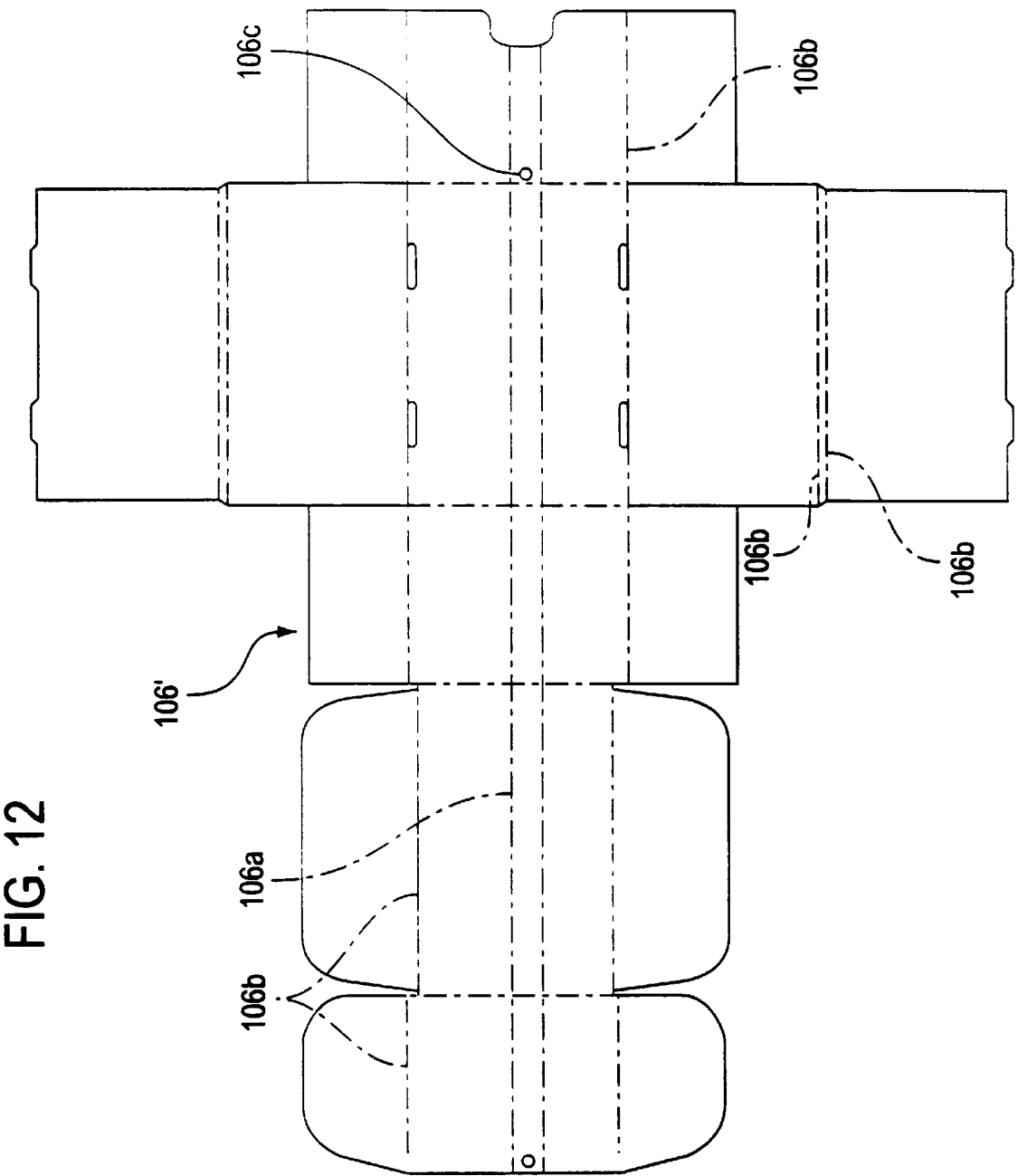
FIG. 12 is a plan view showing the configuration of a cardboard blank, which can be folded into a double-walled box structure that is used to house the rigid foamed plastic container-with-lid arrangement shown in FIG. 1.

A ported thermoregulating plate 108 is disposed in foamed plastic container 100 so as to partition the interior of foamed plastic container 100 into a lower storage chamber 100a, in which syringes 110 are stored, and an upper refrigerant chamber 100b, in which a container 112 of solid refrigerant (forming a coolant pack) is disposed. As is best seen in FIG. 9, ported thermoregulating plate 108 is formed with two ports or openings 108a at opposite ends thereof.

Figure 3:
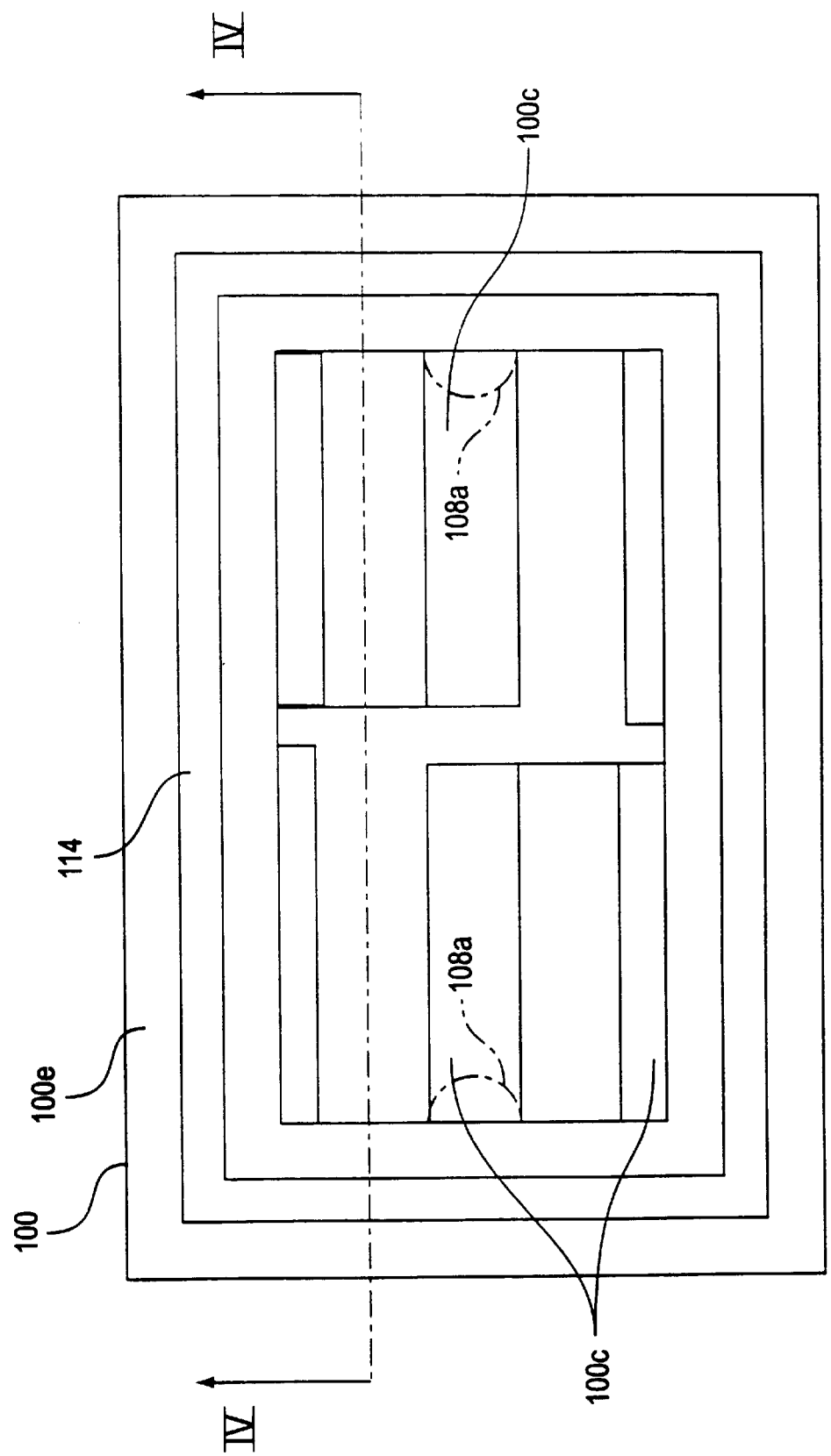
FIG. 3 is a plan view of the rigid foamed plastic container depicting the layout of the support/partition members, and showing a recess or channel which cooperates with a lid.
Figure 4:
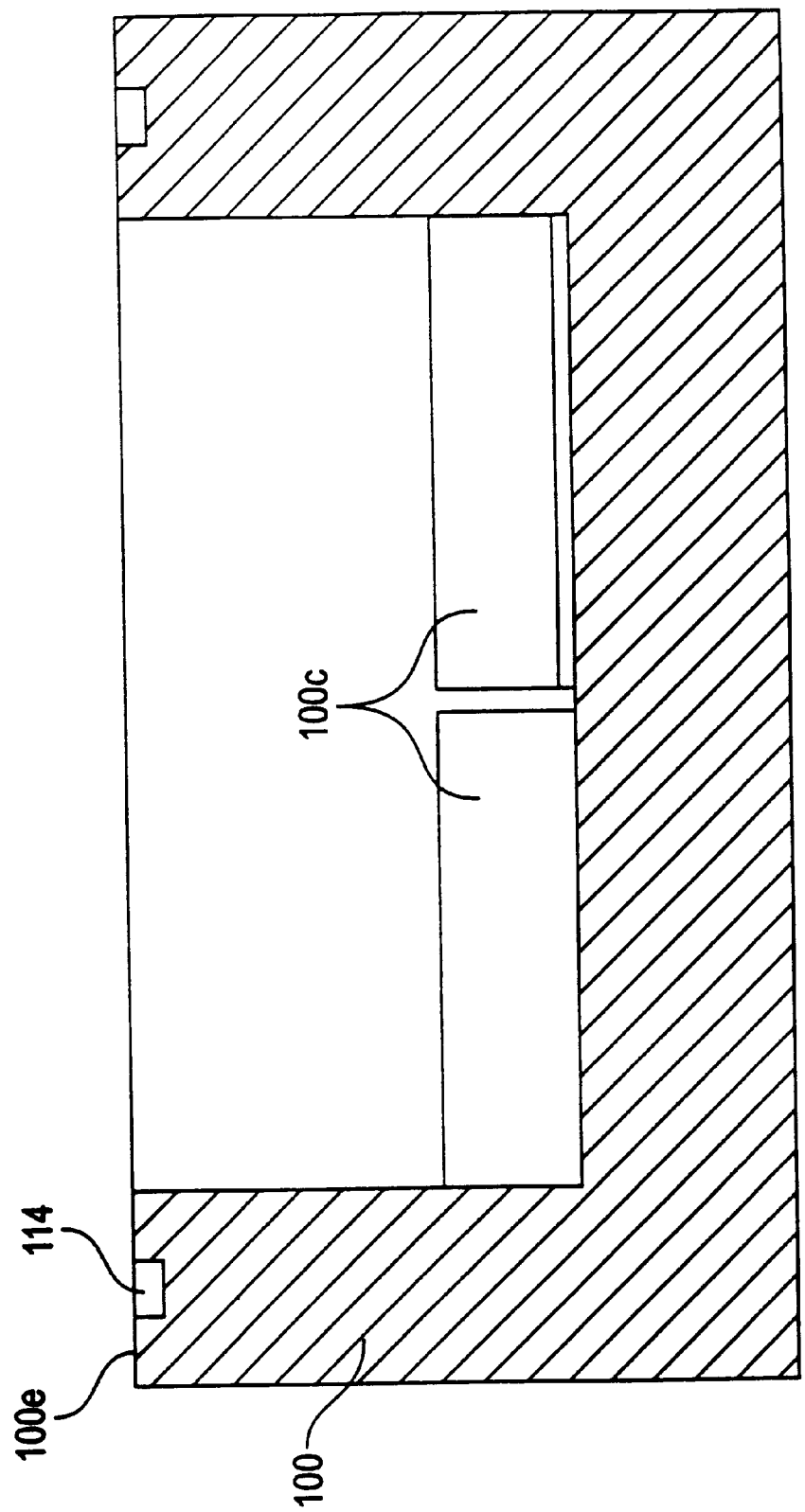
FIG. 4 is a side sectional view taken along section line IV—IV of FIG. 3, showing details of the interior of the rigid foamed plastic container and the support/partition members, which are used to maintain at least one semen storage device in position during transit.
Figure 5:
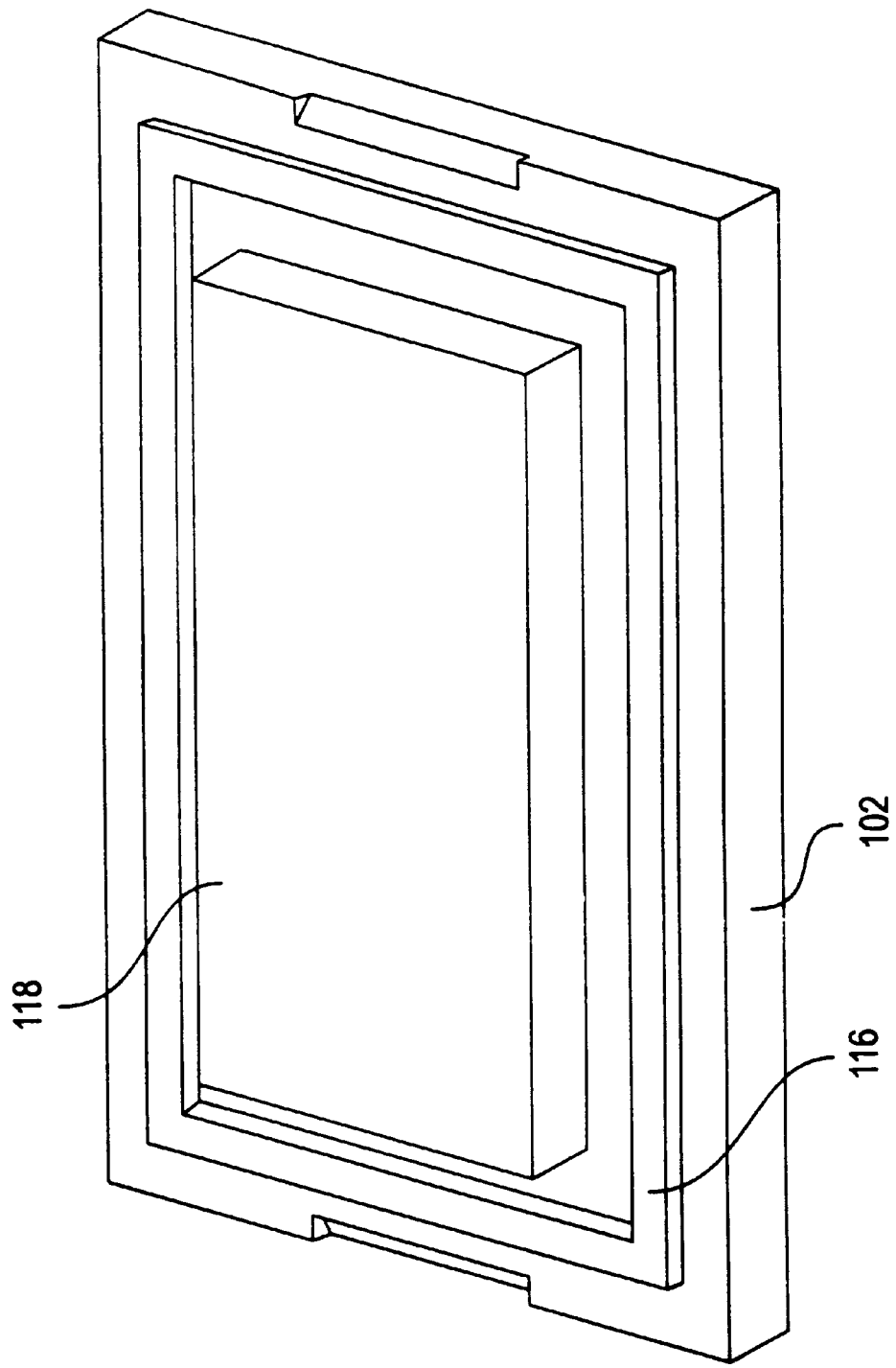
FIG. 5 is a perspective view of the lid that is used to close the rigid foamed plastic container depicted in FIGS. 1–4.
Figure 6:
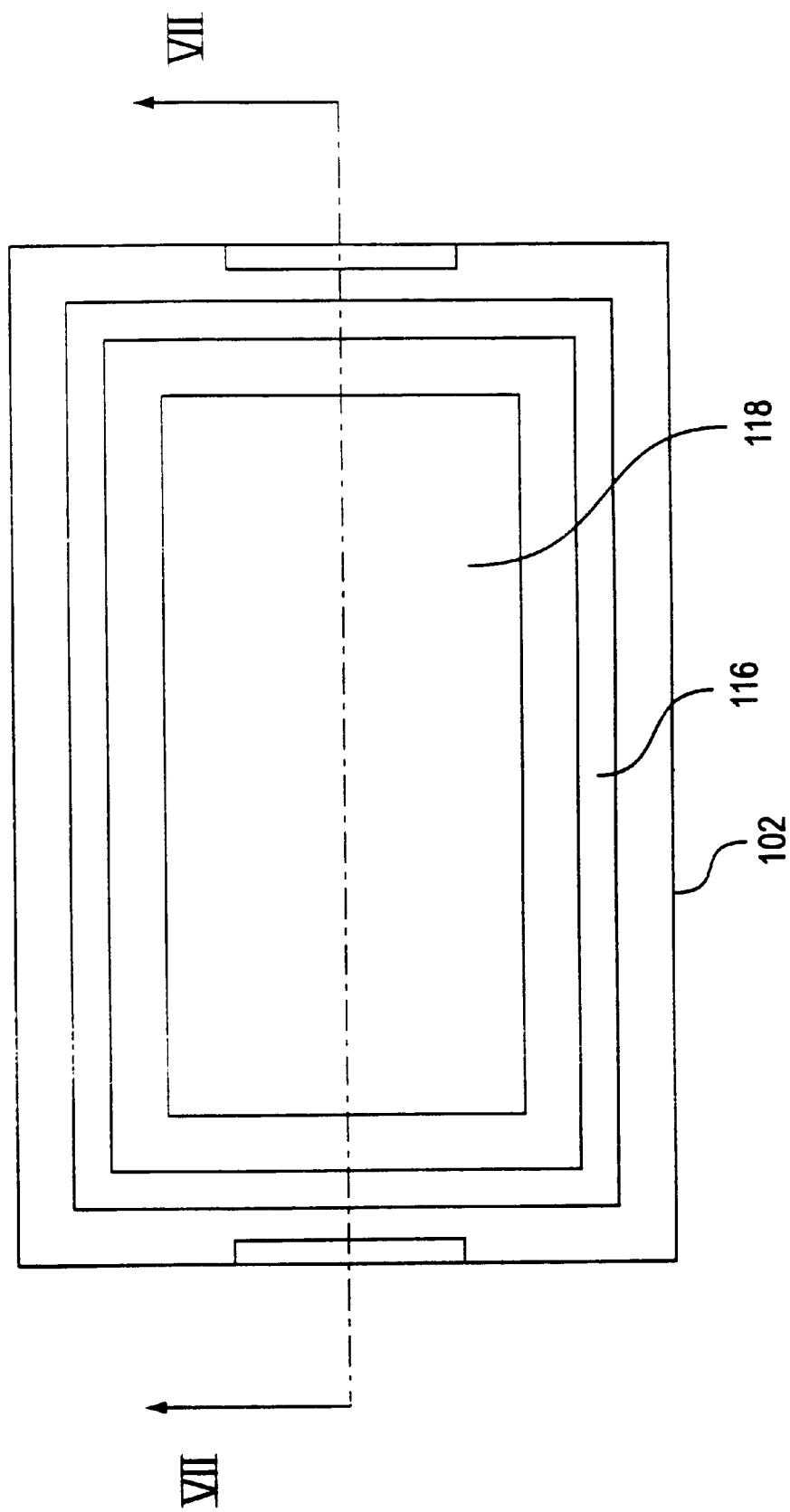
FIG. 6 is a plan view showing the underside of the lid depicted in FIG. 5.
Figure 7:
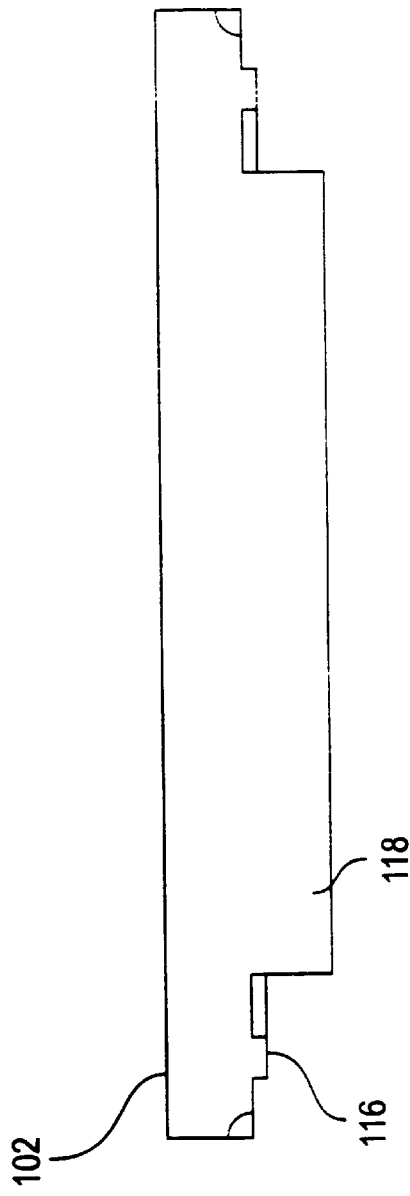
FIG. 7 is a sectional view taken along section line VII—VII of FIG. 6.
Figure 8:
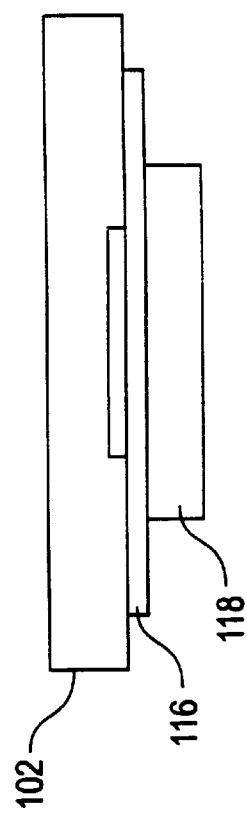
FIG. 8 is an end view of the lid showing the provision of recesses, which facilitate the opening of the rigid foamed container upon arrival as a destination.
Figure 10:
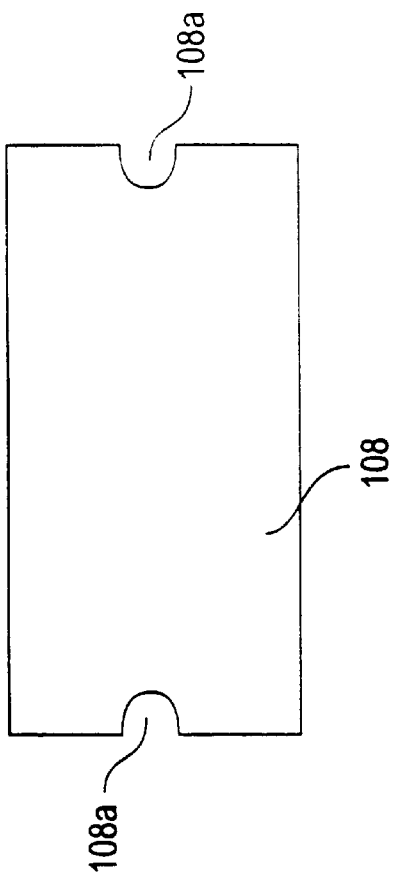
FIG. 10 is a plan view of the thermoregulating plate depicted in FIG. 9.
Figure 11:
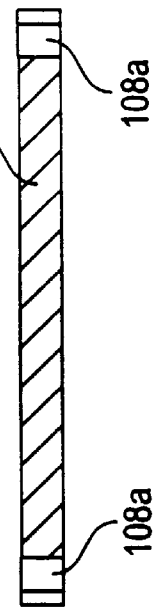
FIG. 11 is a sectional view taken along section line XI—XI of FIG. 10.

As is best seen in FIG. 3, the bottom portion of the interior of foamed plastic container 100 is provided with baffles/ribs/supports/partitions 100c, which are spaced and arranged to support syringes 110 in a rattle free state for smooth transportation, as well as one that interacts with ports of the thermoregulating plate in the manner discussed below.

As is shown by broken lines (ports) 108a in FIG. 3, the ports are formed in thermoregulating plate 108 in a location such that, when in position, each port is located atop a baffle/web/ribbing/support/partition that forms syringe receiving recesses within the bottom of foamed plastic container 100. This arrangement promotes restriction for fluid communication between upper and lower chambers 100a, 100b. Ports 108a are shaped so as to serve as openings into which digits, such as the fingers of an operator, can be inserted to facilitate removal of the thermoregulating plate when quick and easy access to one or more syringes in the lower chamber 100a is desired.

In accordance with the present invention, thermoregulating plate 108 can, if so desired, be made slightly smaller than the interior dimensions of the interior of container 100, thus permitting small clearances between the side walls of the interior of the foamed plastic container and the edges of the thermoregulating plate. This facilitates access to the syringes by promoting facile removal of the thermoregulating plate. However, excessive communication between upper and lower chambers 100b, 100a should be avoided in order to decrease convective flows therebetween.

Container 100, lid 102, and thermoregulating plate 108 preferably may be formed of a rigid highly thermal insulating foam plastic, such as polystyrene or polyurethane foam, which is expanded to 2.0 lbs./square inch. The thermoregulating plate 108 is preferably about one-half to two inches thick. These values of thickness and density were found to provide appropriate insulation, and to optimize the upper/lower chamber division, upper/lower chamber fluid restriction, and ease-of-use effects of the plate.

As is shown in FIGS. 1–4, container 100 is formed with a continuous channel 114 about its upper edge 100e. As shown in FIGS. 5–8, lid 102 is formed with a continuous ridge 116, which is adapted to be snugly received in channel 114 when lid 102 is placed on top of container 100. Lid 102 is further formed with a central boss portion 118, which fits snugly into the open mouth of container 100.

This lid arrangement allows container 100 to be simply and easily closed off with only a minimum of external ambient moisture being subsequently permitted to enter the container.

In this preferred embodiment, the corrugated cardboard or fiberboard box 106, in which container and lid 100, 102 are disposed, is a double walled arrangement, which inherently adds to the thermal insulation to further isolate the container from the effects of ambient temperature and/or ambient temperature fluctuation. Furthermore, as mentioned above, this box also can act a wick to absorb moisture during transit.

Accordingly, when box 106 is closed, sealed, and ready for transportation, it serves not only to protect container 100 against compressive forces, but also adds additional thermal insulation. Furthermore, box 106 provides a wicking effect to absorb water/moisture, which thus creates a type of vapor barrier or trap that assists in maintaining the interior of the container free of condensation.

The construction of cardboard box 106 is also unique in that it has a configuration such that, unlike conventional cardboard boxes, it has only one site or opening via which access to the interior thereof can be gained. In addition, cardboard box 106 has a security plastic strip 106a that is buried from one end to the other of the cardboard blank 106' during its manufacture, as is shown in phantom in FIG. 12 before its being folded along chain lines 106b. When folded into its operative configuration, box 106 is thus closed and sealed in a manner which renders it essentially impossible for the contents to be tampered with without the recipient of the package being aware of same.

More specifically, two openings 106c are formed in two opposite ends of blank 106' within the end regions of embedded security plastic strip 106a. When blank 106' is folded along the dotted lines shown in FIG. 12 to form a box, openings 106c are located adjacent one another so that a lead, or similar member of a seal, can be passed through the openings. Upon the ends of such a lead being permanently connected to one another, such as by crimping, fusing, bonding, or the like, the interior of the box cannot be accessed, while the seal remains intact, without destroying at least a portion of the cardboard. Thus, this embodiment prevents anyone from secretly tampering with the contents of the box.

This box finds highly advantageous to use, according to the present invention, in that it is simultaneously lightweight and inexpensive, it provides increased thermal insulation, it acts as a vapor trap or barrier, and it can be conveniently discarded or disposed of after a single use. Furthermore, the double wall structure, which results after fully folding blank 106', results in a remarkably robust box that provides a high degree of structural strength and protection for the foam plastic container held within during transit. These properties prevent breakage/damage by the inevitable bumping and jostling which occurs during handling by commercial courier or postal services, especially during loading/unloading from one transport vehicle to another, such as at truck terminals, airports, train stations, and the like.

It will be noted that the use of the above described corrugated cardboard box is not necessarily limited to application with thermally insulated foam plastic container 100, and can be used to ship other items and products, e.g., electronics. In other words, the cardboard box of the instant invention can be purchased as a blank, and subsequently folded, loaded, and sealed in a manner which permits the dispatch of a variety of items in a secure and inexpensive manner.

In order to achieve successful shipping of delicate semen cargo, it is preferred to place a specimen of gel-free semen from all ejaculates in an incubator at about 37° C. within about 2 minutes of collection. The sperm concentration is then measured using a densimeter. Immediately thereafter, the semen sample is mixed with a dual sugar, pH adjusted semen extender already in the syringe(s) and at room temperature by drawing the semen sample into the syringe (s). Each syringe is then capped with a sterile cap 110a, and placed in position in the bottom of container 100. Thermoregulator plate 108 is then placed in position over top syringes 110 in the manner shown in FIG. 1. Coolant pack 112 then is placed on top of thermoregulating plate 108 and lid 102 is fitted into position to close container 100. The closed container is then placed in the corrugated cardboard shipping container, which is then sealed closed, including use of security plastic strip 106a with holes 106c.

Tables 1 and 2 show results of tests conducted on three prior art devices, as well as the present invention. In Tables 1 and 2, PRIOR ART 1, PRIOR ART 2, and PRIOR ART 3 represent the devices sold as Equitainer™, ExpectaFoal™, and Equine Express™, respectively. As will be appreciated by the skilled artisan, the unexpected and superior performance of the present invention over the performance of other prior art devices is self-evident. In particular, the present invention provided a suitable slow cooling rate in the temperature ranges of about 16–14° C. and about 14–12° C., as is clearly shown in Table 1. Furthermore, practice according to the present invention resulted in the greatest time to reach the lowest temperature, compared to all other arrangements tested (Table 2). Regardless of the extended time to reach the ultimate storage temperature, the time over which the semen could be maintained below 15° C. (77 hours) was greater with the present invention than with the other arrangements tested (Table 2, last column), based on parameters such as the motility of spermatozoa (total motility, progressive motility, rapid motility, curvilinear velocity, straight line velocity, etc.).

TABLE 1

EFFECT OF EQUINE SEMEN TRANSPORT CONTAINER ON COOLING RATES
(IN DEGREES CELSIUS PER MINUTES) OF 40-ml ALIQUOTS OF EXTENDED SEMEN

| Container | 20 to 18° C. | 18 to 16° C. | 16 to 14° C. | 14 to 12° C. | 12 to 10° C. | 10 to 8° C. |
| --- | --- | --- | --- | --- | --- | --- |
| Prior Art 1 | −0.09 | −0.08 | −0.06 | −0.05 | −0.04 | −0.02 |
| Prior Art 2 | −0.12 | −0.12 | −0.12 | −0.12 | −0.11 | −0.07 |
| Prior Art 3 | −0.11 | −0.10 | −0.10 | −0.04 | −0.02 | −0.003 |
| Invention | −0.0899 | −0.0714 | −0.0525 | −0.0342 | −0.0177 | −0.0025 |

TABLE 2

EFFECT OF EQUINE SEMEN TRANSPORT CONTAINER ON STORAGE TEMPERATURES
AND WARMING RATES OF 40-ML ALIQUOTS OF EXTENDED SEMEN
(IN DEGREES CELSIUS PER MINUTE)

| Container | Lowest Temperature During Storage (° C.) | Time Required to Obtain Lowest Storage Temperature | Time Required for Semen Temperature to Exceed 10° C. | Time Required for Semen Temperature to Exceed 15° C. |
| --- | --- | --- | --- | --- |
| Prior Art 1 | 5.5 | 11.25 h | 53.0 h | 71.0 h |
| Prior Art 2 | −0.1 | 8.5 h | 27.5 h | 32.5 h |
| Prior Art 3 | 7.9 | 17.5 h | 33.5 h | 45.25 h |
| Invention | 8.4 | 22.7 h | 59.0 h | 77.0 h |

The foregoing description of preferred embodiments of the present invention have been presented only for purposes of illustration and description. It is not intended to be exhaustive or to limit the invention to the precise disclosed forms. Many obvious modifications and variations of the disclosed preferred embodiments will be apparent to practitioners skilled in this art. Similarly, any process steps described might be interchangeable with other steps in order to achieve the same result. The embodiments were chosen and described to best explain the principles of the invention and its best mode practical application to thereby enable others skilled in this art to understand the invention for various embodiments and with various modifications as are suited to the particular uses contemplated. It is intended that the scope of the invention be defined by the claims appended hereto and their equivalents.

For example, any suitable alternate gram positive and/or gram negative antibiotics may be used in the semen extender solution, as well as any effective broad spectrum antibiotic (s). In addition, security plastic strip 106a of the cardboard box could be replaced with a strip made of a different material. As yet another example, the box could be made of a material other than cardboard, or a combination of cardboard and another material. As a further example, the ribbing/support/partition members in the bottom of the foamed plastic container need not necessarily extend the greater part of the length of the bottom of the rigid foamed plastic container, provided that (1) the plastic syringe(s) or other semen storage device(s) were held securely in position, and (2) the ports of the thermoregulating plate were appropriately "covered" to provide the requisite restriction for fluid communication between the upper and lower chambers of the bottom of the rigid foamed plastic container. In addition, the rigid foamed plastic container could be made of a material(s) different from that of the instant invention, provided that roughly similar insulating/heat transfer characteristics obtained for the final product and the above-described relatively slower cooling rate is not comprised. As an even further example, a semen extender solution with a composition different from that described herein (e.g., Kenny extender) could be used, provided the degree of dilution approximated a value or range of values that at least overlapped the range provided by the instant invention. As another example, storage and transport devices that are made of materials different from those disclosed herein would fall within the scope of the present invention, provided that they effectively promoted semen storage, including being sterile and containing no spermicidal compounds. As a final example, use of the instant invention for storage and transport of equine semen samples need not be so limited. Other biological (including semen from other animal sources) and non-biological samples requiring similar cooling rates and/ or storage temperatures will benefit from practice of the disclosure herein. Furthermore, the principles of the present invention can be applied to create similar container arrangements, but with adaptations for the different cooling rate or other parameter that is required to meet the needs of the particular biological or non-biological product undergoing storage and/or transport.

What is claimed is:

1. A container arrangement for transporting semen, comprising:
    at least one semen storage device for storing semen;
    a rigid foamed plastic container comprising:
        an interior with a bottom;
        a floor located on the bottom of the interior;
        at least one support member contoured to support the at least one semen storage device;
        an upper end; and
        an upper edge located at the upper end and containing a recess therein extending continuously thereabout for receiving at least one ridge extending from a lid for closing the upper end of the rigid foamed plastic container in a manner which forms a seal when the lid is pressed onto the upper end of the rigid foamed plastic container;
    a refrigerant pack containing a solid foam coolant; and
    a separating means disposed in the interior of the rigid foamed plastic container for separating the at least one semen storage device from the refrigerant pack and for limiting the cooling rate of the at least one semen storage device, when containing an semen sample, to no more than about 0.20° C./min over at least the temperature range of about 38° C. to about 5° C.

2. The container arrangement as set forth in claim 1, wherein the separating means comprises
    a ported thermoregulating plate for the purpose of partitioning the interior into a lower chamber in which the at least one support member is formed, and in which the at least one semen storage device is supported, and
    an upper chamber in which the refrigerant pack containing the solid foam coolant is disposed,
    wherein the thermoregulating plate has first and second ports formed therein, the first and second ports are formed at opposite ends of the thermoregulating plate, and the first and second ports are arranged to overlay the at least one support member in a manner that closes each port so as to restrict fluid communication between the upper and lower chambers.

3. The container arrangement as set forth in claim 2, wherein the first and second ports are dimensioned to permit the insertion of human digits to additionally permit the thermoregulating plate to be quickly and easily lifted to allow access to the at least one semen storage device in the lower chamber.

4. The container arrangement as set forth in claim 1, wherein the at least one semen storage device is selected from the group consisting of plastic syringes and polypropylene tubes with caps.

5. The container arrangement as set forth in claim 1, wherein the semen is extended by dilution with an extender solution comprising sucrose, glucose, non-fat dry milk solids, and at least first and second selected antibiotics, wherein the first antibiotic is effective against gram negative bacteria, and the second antibiotic is effective against gram positive bacteria.

6. The container arrangement as set forth in claim 4, wherein the at least one semen storage device contains from about a 10 ml aliquot to about a 225 ml aliquot of extender solution.

7. The container arrangement as set forth in claim 4, wherein, prior to introduction of an equine semen sample, the semen storage device contains a volume of extender solution sufficient to dilute the semen sample from about 3:1 to about 10:1 (v/v).

8. The container arrangement as set forth in claim 4, wherein, prior to introduction of an equine semen sample, the semen storage device contains a volume of extender solution sufficient to dilute the semen sample from about 6:1 to about 10:1 (v/v).

9. The container arrangement as set forth in claim 1, wherein the rigid foamed plastic container with lid in place is snugly enclosed within an inside of a corrugated cardboard box.

10. The container arrangement as set forth in claim 1, wherein the separating means limits the cooling rate of the at least one semen storage device, when containing an equine semen sample, to no more than about 0.10° C./min over at least the temperature range of about 38° C. to about 5° C.

11. The container arrangement as set forth in claim 1, wherein the separating means limits the cooling rate of the at least one semen storage device, when containing an equine semen sample, to no more than about 0.20° C./min over at least the temperature range of about 15° C. to about 5° C.

12. The container arrangement as set forth in claim 1, wherein the separating means limits the cooling rate of the at least one semen storage device, when containing an equine semen sample, to no more than about 0.10° C./min over at least the temperature range of about 15° C. to about 5° C.

13. A container arrangement for transporting equine semen comprising:
  a recyclable rigid foamed plastic container comprising:
    an interior with a bottom;
    a floor located on the bottom of the interior;
    at least one support member contoured to support at least one semen storage device containing extended equine semen;
    an upper end; and
    an upper edge located at the upper end and containing a recess therein extending continuously thereabout for receiving at least one ridge extending from a lid which forms a seal when the lid is pressed onto the upper end of the rigid foamed plastic container;
  a ported thermoregulating plate disposed in the interior of the recyclable rigid foamed plastic container for partitioning the interior into
  a lower chamber in which the at least one support member is formed, and in which the at least one semen storage device is supported,
  an upper chamber in which a refrigerant pack containing a solid foam coolant is disposed, wherein the thermoregulating plate has first and second ports formed therein, the first and second ports are formed at opposite ends of the thermoregulating plate arranged to overlay the at least one support member in a manner that closes each port so as to restrict fluid communication between the upper and lower chambers; and
  a corrugated cardboard box snugly enclosing the rigid foamed plastic container with lid in place.

14. The container arrangement as set forth in claim 13, wherein the ported thermoregulating plate is selected to attenuate the rate of cooling of the extended equine semen contained in the at least one semen storage device to no more than 0.20° C./min over a temperature range of about 38° C. to about 5° C.

15. The container arrangement as set forth in claim 13, wherein the at least one semen storage device is selected from the group consisting of plastic syringes and polypropylene tubes with caps.

16. The container arrangement as set forth in claim 13, wherein the extended equine semen is prepared by diluting an equine semen sample with an extender solution comprising sucrose, glucose, non-fat dry milk solids, and at least first and second selected antibiotics, wherein the first antibiotic is effective against gram negative bacteria, and the second antibiotic is effective against gram positive bacteria.

17. A method of transporting equine semen comprising the steps of:
  mixing an extender solution with a sample of equine semen to form an extended semen mixture, wherein the extender solution has a pH and an osmolality, each of which has been previously adjusted to within a respective predetermined range;
  introducing at least a portion of the extended semen mixture into at least one semen storage device and capping the semen storage device;
  placing the at least one semen storage device on at least one support member provided therefore in the bottom of a rigid foamed plastic container, wherein each support member is contoured to accept at least one semen storage device;
  placing a ported thermoregulating plate in the rigid foamed plastic container in a manner which partitions the interior of the container into a lower compartment in which the semen storage device is disposed, and an upper compartment in which a refrigerant pack containing a solid foam coolant is disposed, wherein the thermoregulating plate is formed of a rigid foamed plastic, and overlays the at least one support member formed in the bottom of the rigid foamed plastic container in a manner that closes each port so as to restrict fluid communication between the upper and lower chambers;
  applying a lid to the rigid foamed plastic container in a manner that closes an upper end of the rigid foamed plastic container, wherein the lid comprises a rigid foamed plastic material, at least one sealing rib which extends about a lower surface of the lid that is snugly received in a recess which extends continuously about the upper end of the rigid foamed plastic container; and
  enclosing the rigid foamed plastic container with the lid closed in place in a corrugated cardboard box.

18. The method as set forth in claim 17, wherein, prior to introduction of an equine semen sample, the semen storage device contains a volume of extender solution sufficient to dilute the semen sample from about 3:1 to about 10:1 (v/v).

19. A container arrangement comprising:
  a single corrugated cardboard blank adapted to be folded into a double-walled box having a single site of entry;
  a plastic strip embedded in the cardboard blank and extending a full length of the blank;
  first and second holes formed in the blank in a manner wherein the first and second holes pass through the plastic strip, and are located proximate first and second ends of the cardboard blank; and
  the first and second holes are located proximate one another when the double-walled corrugated cardboard blank is folded into its box configuration in a manner that permits a lead to be passed therethrough to enable the double-walled corrugated box to be locked against unauthorized entry.

20. A container arrangement as set forth in in claim 19, further comprising:
  a rigid foamed plastic container comprising a support structure contoured to support at least one semen storage device;
  a lid for closing an open upper end of the rigid foamed plastic container, the lid being formed with at least one ridge that extends continuously about a lower surface of the lid proximate an edge of the lid, the ridge being adapted to be received in a recess which extends continuously about the upper edge of the rigid foamed plastic container in a manner which forms a seal when the lid is pressed onto the rigid foamed plastic container;
  a refrigerant pack containing a solid foam coolant; and
  means disposed in said container for partitioning the interior of the rigid foamed plastic container, separating the at least one semen storage device and the refrigerant pack, and for limiting the cooling rate of contents in the vessel to a value not greater than about 0.10° C./min.

* * * * *